United States Patent [19]

Bourguignon et al.

[11] Patent Number: 5,276,036

[45] Date of Patent: Jan. 4, 1994

[54] 3-(N-AZABICYCLOALKYL)AMINOPYRIDAZINE DERIVATIVES AND PHARMACEUTICAL COMPOSITIONS IN WHICH THEY ARE PRESENT

[75] Inventors: Jean-Jacques Bourguignon, Hipsheim; Jean-Paul Kan, Clapiers; Camille G. Wermuth, Strasbourg, all of France

[73] Assignee: Elf Sanofi, Paris, France

[21] Appl. No.: 883,168

[22] Filed: May 15, 1992

[30] Foreign Application Priority Data

May 16, 1991 [FR] France .................. 91 05973

[51] Int. Cl.⁵ .................. A61K 31/50; C07D 237/20
[52] U.S. Cl. .................. 514/253; 514/227.8; 514/236.5; 514/247; 514/252; 544/58.5; 544/114; 544/224; 544/238
[58] Field of Search .................. 514/252; 544/238

[56] References Cited

U.S. PATENT DOCUMENTS

| | | | |
|---|---|---|---|
| 4,508,720 | 4/1985 | Kan et al. | 514/247 |
| 4,624,952 | 11/1986 | Biziere et al. | 514/252 |
| 4,721,711 | 1/1988 | Chambon | 514/238 |
| 5,081,119 | 1/1992 | Boigegrain | 514/247 |
| 5,112,825 | 5/1992 | Stokbroekx et al. | 514/252 |

FOREIGN PATENT DOCUMENTS 382634 8/1990 European Pat. Off. ............ 544/238

OTHER PUBLICATIONS

Wermuth, Jour. Med. Chem. vol. 32 pp. 528-537 (1989).

*Primary Examiner*—Donald G. Daus
*Attorney, Agent, or Firm*—Bacon & Thomas

[57] ABSTRACT

The invention relates to 3-aminopyridazine derivatives. These compounds have the formula

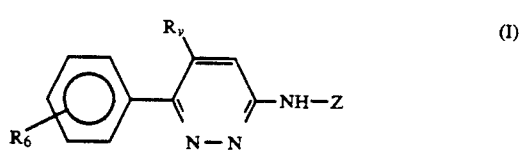

(I)

in which:

$R_V$ is a linear or branched $C_1$-$C_4$ alkyl group;
$R_6$ is hydrogen, a $C_1$-$C_3$ alkoxy or a hydroxyl group; and
Z is a group

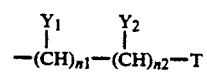

in which:
$n_1$ and $n_2$ independently are zero or one,
$Y_1$ and $Y_2$ independently are hydrogen or a $C_1$-$C_3$ alkyl group, and
T is a dialkylamino group in which the alkyls are $C_1$-$C_3$, if $Y_1$ or $Y_2$ is other than hydrogen, or T is a heterocycle selected from:

a) 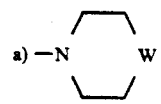 when $n_1 = n_2 = 1$
$Y_1$ = CH$_3$ and $Y_2$ = H or
$Y_1$ = H and $Y_2$ = CH$_3$
and W is an oxygen or sulfur atom b) 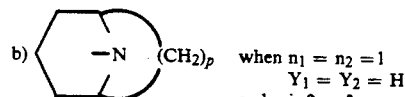 when $n_1 = n_2 = 1$
$Y_1 = Y_2 = H$
and p is 2 or 3;

c) 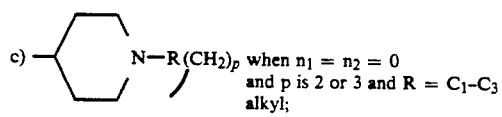 when $n_1 = n_2 = 0$
and p is 2 or 3 and R = $C_1$-$C_3$ alkyl;

d) 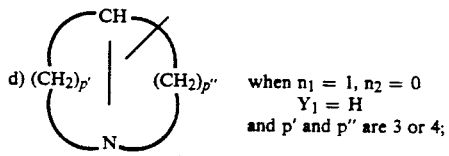 when $n_1 = 1, n_2 = 0$
$Y_1$ = H
and p' and p'' are 3 or 4;

Application: drugs active on the central nervous system.

7 Claims, No Drawings

3-(N-AZABICYCLOALKYL)AMINOPYRIDAZINE DERIVATIVES AND PHARMACEUTICAL COMPOSITIONS IN WHICH THEY ARE PRESENT

The present invention relates to 3-aminopyridazine derivatives active on the central nervous system.

Numerous pyridazine derivatives have been proposed as drugs active especially on the cardiovascular system or on the central nervous system.

More particularly, French patent application A-2510998 and European patent application A-72726 describe variously substituted pyridazines which all carry in the 3-position an amine substituent of the type $$-NH-Alkylene-N\begin{matrix}X\\ \\Y\end{matrix}$$

in which X and Y independently are hydrogen or an alkyl group or form, with the nitrogen atom to which they are bonded, a heterocycle such as morpholine. These compounds are active on the central nervous system as antidepressants.

According to the present invention, novel 3-aminopyridazine derivatives have now been found which are devoid of antidepressant activity but are active as ligands for the cholinergic receptors, more particularly as ligands for the $M_1$ muscarinic receptors.

The present invention therefore relates to pyridazines of the formula (I)

in which:

$R_V$ is a linear or branched $C_1$-$C_4$ alkyl group;
$R_6$ is hydrogen, a $C_1$-$C_3$ alkoxy or a hydroxyl group; and
Z is a group $$\begin{matrix}Y_1 & Y_2\\ | & |\\ -(CH)_{n1}-(CH)_{n2}-T\end{matrix}$$

in which:

$n_1$ and $n_2$ independently are zero or one,
$Y_1$ and $Y_2$ independently are hydrogen or a $C_1$-$C_3$ alkyl group, and
T is a dialkylamino group in which the alkyls are $C_1$-$C_3$, if $Y_1$ or $Y_2$ is other than hydrogen, or T is a heterocycle selected from:

a) $-N\overbrace{\phantom{XXX}}W$  when $n_1 = n_2 = 1$
    $Y_1 = CH_3$ and $Y_2 = H$ or
    $Y_1 = H$ and $Y_2 = CH_3$
    and W is an oxygen or sulfur atom b) bicyclic ring with $-N$ and $(CH_2)_p$  when $n_1 = n_2 = 1$
    $Y_1 = Y_2 = H$
    and p is 2 or 3;

c) bicyclic ring with $N-R(CH_2)_p$  when $n_1 = n_2 = 0$
    and p is 2 or 3 and $R = C_1$-$C_3$ alkyl;

d) $(CH_2)_{p'}$ — CH — $(CH_2)_{p''}$ with N  when $n_1 = 1, n_2 = 0$
    $Y_1 = H$
    and p' and p'' are 3 or 4;

and their salts with organic or mineral acids.

The preferred compounds of the invention are those in which:

either $n_1$ and $n_2$ are equal to one, $Y_1$ and $Y_2$ are each a methyl or a hydrogen and T is a dialkylamino group in which the alkyls are $C_1$-$C_3$;

or $n_1$ and $n_2$ are equal to one, $Y_1$ is a methyl and $Y_2$ is hydrogen, or $Y_1$ is hydrogen and $Y_2$ is a methyl, and T is a group a);

or $n_1$ and $n_2$ are equal to one, $Y_1$ and $Y_2$ are hydrogen and T is the heterocycle b);

or $n_1$ and $n_2$ are equal to zero and T is the heterocycle c);

or $n_1$ is equal to one and $n_2$ is equal to zero, $Y_1$ is hydrogen and T is the heterocycle d);

and their salts with mineral or organic acids.

The salts of the compounds of formula (I) according to the present invention include those with mineral or organic acids which permit a suitable separation or crystallization of the compounds of formula (I), such as picric acid or oxalic acid, as well as those with mineral or organic acids which form pharmaceutically acceptable salts such as the hydrochloride, hydrobromide, sulfate, hydrogensulfate, dihydrogenphosphate, methanesulfonate, maleate, fumarate and naphthalene-2-sulfonate.

According to another feature, the present invention relates to a method of preparing the compounds of formula (I).

This method comprises reacting an amine of the formula $$H_2N-Z \qquad (II)$$

in which Z is as defined above for (I), with the 3-chloropyridazine of the formula (III)

in which $F_V$ and $R_6$ are as defined above for (I), and, if desired, converting the resulting compound to a salt with a mineral or organic acid.

The substitution reaction of the 6-chloropyridazine (III) with the amine (II) is carried out at a temperature of between 100° and 150° C., without a solvent or in the presence of an inert solvent such as an alkanol, and, if appropriate, in the presence of ammonium chloride. The compound (I) is then isolated and purified by the usual methods. The resulting product is isolated in the form of the free base or a salt by the conventional techniques.

When the compound of formula (I) is obtained in the form of the free base, salt formation is effected by treatment with the chosen acid in an organic solvent. Treatment of the free base, dissolved for example in an alcohol such as isopropanol, with a solution of the chosen acid in the same solvent gives the corresponding salt, which is isolated by the conventional techniques. The hydrochloride, hydrobromide, sulfate, hydrogen-sulfate, dihydrogenphosphate, methanesulfonate, methylsulfate, oxalate, maleate, fumarate and naphthalene-2-sulfonate, for example, are prepared in this way.

When the reaction is complete, the compound of formula (I) can be isolated in the form of one of its salts, for example the hydrochloride; in this case, if necessary, the free base can be prepared by neutralization of said salt with an inorganic or organic base such as sodium hydroxide or triethylamine, or with an alkali metal carbonate or bicarbonate such as sodium or potassium carbonate or bicarbonate.

When the compounds (I) possess a chiral center and are obtained in the form of racemates, which can be separated according to conventional techniques, the corresponding enantiomers form part of the invention.

The 6-chloropyridazines (III) used as starting materials are prepared from the 2H-pyridazin-3-ones of the formula (IV)

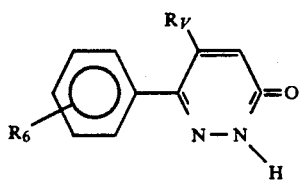
(IV)

by reaction with excess phosphorus oxychloride under the action of heat, without a solvent or in the presence of an inert solvent such as, for example, acetonitrile.

The 2H-pyridazin-3-ones (IV) are known or are prepared by known methods in accordance with the following reaction scheme:

SCHEME 1

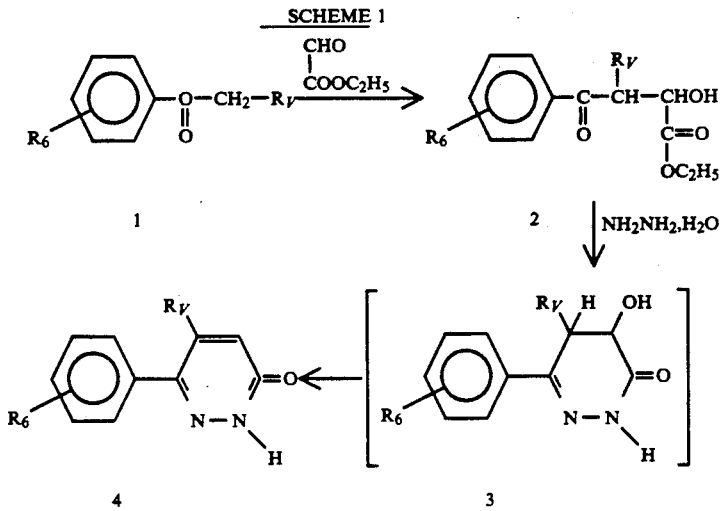

The aldolization reaction of an acetophenone derivative 1 with ethyl glyoxylate makes it possible to prepare the hydroxyketoester 2; this is then cyclized with hydrazine hydrate to give the compound 3, which is not isolated.

The hydroxyketoester 2 is converted to the pyridazone 4 in a single step combining cyclization with dehydration.

The amines $H_2N-Z$ (II) are known or have been prepared by known methods.

The reaction schemes below illustrate the preparation of the amines $H_2N-Z$ (II) without implying a limitation.

When $n_1=n_2=1$, $Y_1=Y_2=H$ and T is the heterocycle b) in which p=2 or 3, the corresponding amine (II) is prepared in accordance with the following reaction scheme:

SCHEME 2

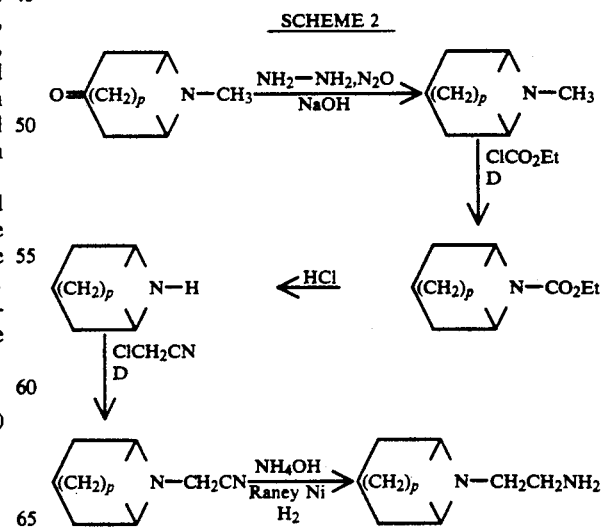

When $n_1=n_2=0$ and T is the heterocycle c), the corresponding amine (II) is prepared by the method described by Dostert et al., Eur. J. Med. Chem. Chim. Ther., 1984, 19, 2, 105-110, in accordance with the following scheme 3, which makes it possible to prepare the compounds (II) in which the —NH₂ group has either the equatorial configuration (IIe) or the axial configuration (IIa).

SCHEME 3
-Configuration of the —NH₂: equatorial

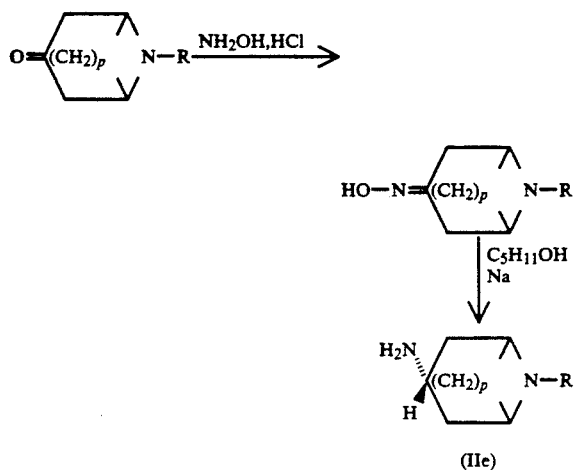

(IIe)

-Configuration of the —NH₂: axial

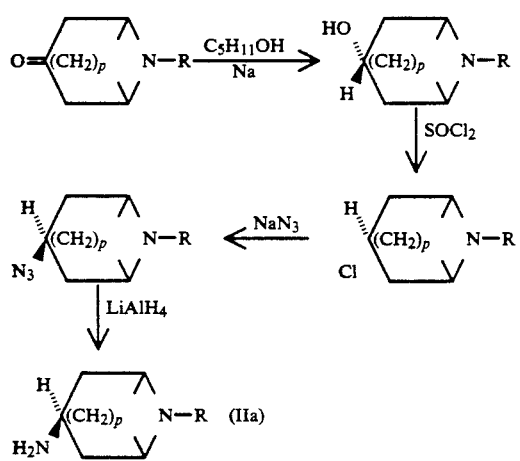

When $n_1=1$, $n_2=0$, $Y_1=H$, $p'=p''=3$ and Z is 1-azabicyclo[3,3,0]octane, i.e. heterocycle d), the corresponding amine, 1-azabicyclo[3,3,0]octyl-2-methylamine, is prepared according to Miyano et al., J. Heterocyclic Chem., 1982, 19, 1465; Miyano et al., Synthesis, 1978, 701; Miyano et al., J. Heterocyclic Chem., 1987, 47, in accordance with the following reaction scheme:

SCHEME 4

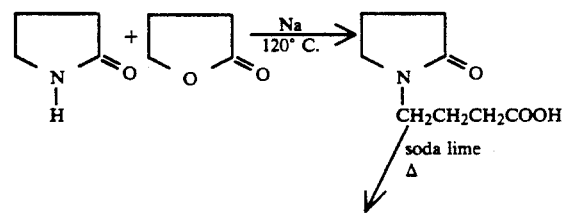

-continued
SCHEME 4

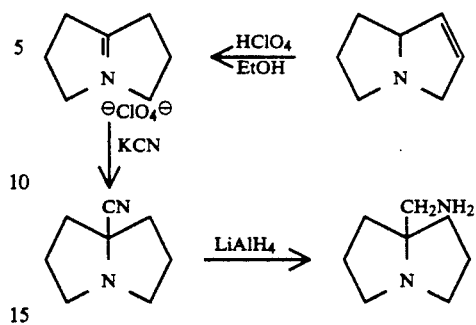

The heterocycle d) can also be prepared according to J. Med. Chem., 1987, 30, 1987, or according to European patent No. 287 356.

When $n_1=n_2=1$, $Y_1=CH_3$, $Y_2=H$ and $T=-N(C_2H_5)_2$, 1-N,N-diethylamino-2-aminopropane is prepared according to an adaptation of the method described by Phillips et al., J. Med. Chem., 1990, 33, 627-633, in accordance with the following reaction scheme:

SCHEME 5

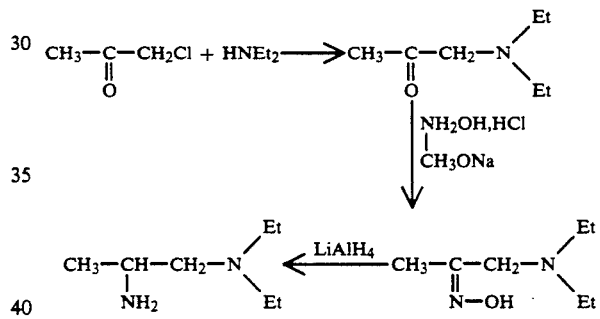

Replacement of the diethylamine with another symmetrical or asymmetrical dialkylamine of formula

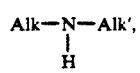

gives the corresponding amines of the formula

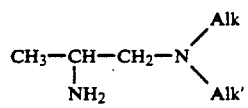

in which Alk and Alk' are $C_1$-$C_3$ alkyls.

Following the operating procedure described in scheme 5 but using as starting products compounds of formulae AlkCOCH₂Cl and Alk-NH-Alk' in which Alk and Alk' are as defined above, the amines of formula (II) are obtained in which $n_1=n_2=1$; $Y_1=Alk$; $Y_2=H$ and T is a dialkylaminogroup.

When $n_1=n_2=1$; $Y_1=H$; $Y_2=Alk$ and T is a dialkylamino group, the amines of formula (II) are obtained by following an operating procedure analogous to that shown in scheme 6 below using an amine of formula

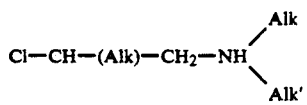

as a starting product.

When $n_1=n_2-1$, $Y_1=H$, $Y_2=-CH_3$ and T is a morpholino or thiomorpholino group, D,L-2-morpholinopropylamine or D,L-2-thiomorpholinopropylamine are prepared in accordance with the following reaction scheme:

SCHEME 6

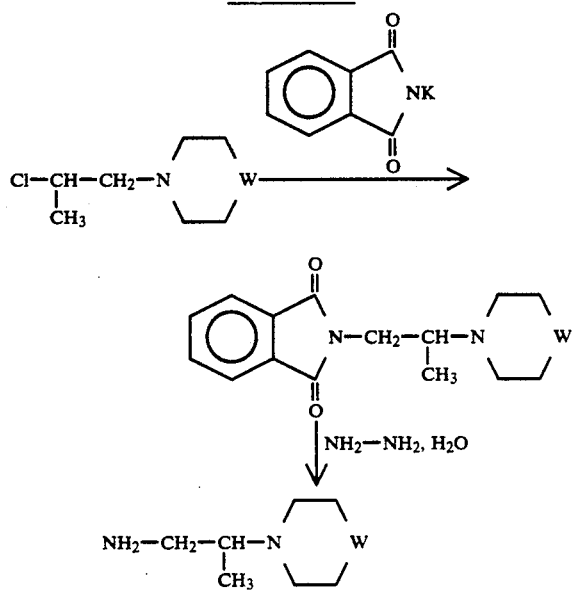

Following the same operating procedure, the amines of formula (II) in which $n_1=n_2=1$; $Y_1=H$; $Y_2=Alk$ (Alk=$C_1$-$C_3$ alkyl) and T represents a morpholino or thiomorpholino group can be prepared using an amine of formula

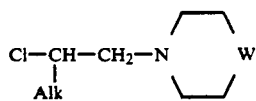

as a starting compound.

The following Examples illustrate the invention without however implying a limitation.

The melting points, m.p., were measured on a Koffler heating bench.

EXAMPLE 1

3-N-(8-Azabicyclo[3,2,1]octyl)ethylamino-6-(2-hydroxyphenyl)-5-methylpyridazine $R_6$ = 2-OH; $R_{\nu}$ = —$CH_3$; $Y_1 = Y_2 = H$;

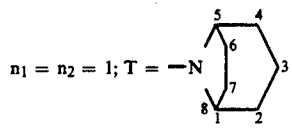

A) 3-N-(8-Azabicyclo[3,2,1]octyl)ethylamino-6-(2-methoxyphenyl)-5-methylpyridazine 1.04 g of N-(8-azabicyclo[3,2,1]octyl)ethylamine, 1.58 g of 3-chloro-5-methyl-6-(2-methoxyphenyl)-pyridazine and 0.38 g of ammonium chloride are dissolved in 2.5 ml of butanol and refluxed for 48 hours under argon. The reaction mixture is concentrated under vacuum and a 20% aqueous solution of potassium carbonate is then added to the residue until the pH is 13. The mixture is extracted with ethyl acetate, the organic phase is separated off by decantation and 30 ml of a 10 % aqueous solution of citric acid are then added. The aqueous phase is separated off, washed with ethyl acetate and rendered alkaline with 30 ml of a 33% aqueous solution of sodium hydroxide. The oil formed is extracted with ethyl acetate and the organic phase is separated off, dried over $Na_2SO_4$, filtered and concentrated under vacuum.

The residue is purified by chromatography on alumina using ethyl acetate and then 9/1 (v/v) ethyl acetate/methanol, with 2% of triethylamine added, as the eluent.

Concentration of the pure product fractions gives 1.2 g of the expected product.

B) 3-N-(8-Azabicyclo[3,2,1]octyl)ethylamino-6-(2-hydroxyphenyl)-5-methylpyridazine 1.2 g of the product obtained above are dissolved in 60 ml of 48% hydrobromic acid and the solution is refluxed for 48 hours. The reaction mixture is concentrated under vacuum and the residue is taken up in a saturated aqueous solution of potassium carbonate. The oil formed is extracted with methylene chloride and the organic phase is separated off, washed with a saturated solution of sodium chloride, dried over $MgSO_4$ and concentrated under vacuum. The residue is triturated in ether and the mixture is filtered and then purified by chromatography on alumina using 8/2 (v/v) ethyl acetate/methanol plus 2% of triethylamine as the eluent. Concentration of the pure product fractions gives 0.8 g of the expected product.

M.p.=208° C.

The compounds listed in Table 1 below are synthesized by following the procedure described in Example 1 and varying the starting 3-chloropyridazine.

TABLE 1

| Example n° | $R_{\nu}$ | Salt | Melting point; °C. |
|---|---|---|---|
| 2 | —$CH_3$ | 2HCl | 226 |
| 3 | —$CH_2CH_2CH_3$ | dioxalate | 150 |

EXAMPLE 4

3-[8-N-Ethylazabicyclo[3,2,1]octyl-3α-amino]-6-phenyl-5-propylpyridazine difumarate $R_6$ = H; $R_{\nu}$ = —$CH_2CH_2CH_3$; $n_1 = n_2 = 0$;

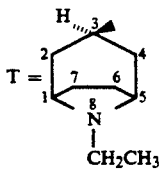

1 g of 3-chloro-6-phenyl-5-propylpyridazine and 1 g of the diamine (IIa) are heated overnight in an autoclave at 160° C. The reaction mixture is taken up in methylene chloride and washed with a saturated aqueous solution of sodium carbonate. The organic phases are decanted, dried over MgSO₄, filtered and concentrated under vacuum. The residue is chromatographed on silica gel using 97/3 (v/v) methylene chloride/methanol as the eluent. Concentration of the pure fractions gives a residue which crystallizes with two equivalents of fumaric acid.

m = 0.44 g.
M.p. = 82° C.

EXAMPLE 5

3-[8-N-Ethylazabicyclo[3,2,1]octyl-3β-amino]-6-phenyl-5-propylpyridazine difumarate $R_6 = H$; $R_{V} = -CH_2CH_2CH_3$; $n_1 = n_2 = 0$;

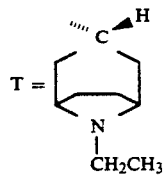

The above compound is prepared by following the procedure of Example 4 and replacing the diamine (IIa) with the diamine (IIe).

m = 0.5 g.
M.p. = 139° C.

EXAMPLE 6

3-(1-Azabicyclo[3,3,0]octyl-2-methylamino)-5-methyl-6-phenylpyridazine difumarate $R_6 = H$; $R_{V} = -CH_3$; $Y_1 = H$; $n_1 = 1$; $n_2 = 0$;

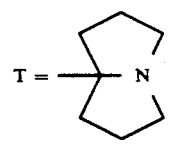

1.52 g of 1-azabicyclo[3,3,0]octyl-2-methylamine, 2.21 g of 3-chloro-5-methyl-6-phenylpyridazine and 0.58 g of ammonium chloride are dissolved in 10 ml of pentanol and refluxed under argon for 24 hours. The reaction mixture is concentrated under vacuum by forming an azeotrope with water. The residue is rendered alkaline with a 10% aqueous solution of potassium carbonate and then extracted with ethyl acetate. The organic phase is separated off and 30 ml of a 10% aqueous solution of citric acid are then added. The aqueous phase is separated off, washed twice with ethyl acetate and rendered alkaline with a 33% solution of sodium hydroxide until the pH is 13. The oil formed is extracted with ethyl acetate and the organic phase is decanted, dried over Na₂SO₄, filtered and chromatographed on alumina using ethyl acetate and then 9/1 (v/v) ethyl acetate/methanol, with 2% of triethylamine added, as the eluent. Concentration of the pure product fractions gives 1 g of the expected product.

0.6 g of the base obtained is dissolved in the minimum amount of acetone, and a solution of 0.45 g of fumaric acid in acetone is then added.

The crystals are filtered off to give 0.1 g of the fumarate.

M.p. = 153.3° C.

The compound below is prepared by following the procedure described in Example 6 and varying the starting 3-chloropyridazine.

TABLE 2

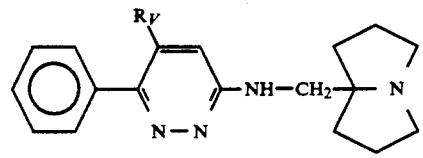

| Example n° | $R_{V}$ | Salt | Melting point; °C. |
|---|---|---|---|
| 7 | —CH₂CH₂CH₃ | difumarate | 179 |

EXAMPLE 8

(RS)-3-N-(1-Diethylaminopropyl-2-amino)-5-methyl-6-phenylpyridazine trifumarate $R_6=H$; $R_{V}=-CH_3$; $n_1=n_2=1$; $Y_1=-CH_3$; $Y_2=H$; $T=-N(C_2H_5)_2$.

1.59 g of 1-N,N-diethylamino-2-aminopropane, 2.49 g of 3-chloro-5-methyl-6-phenylpyridazine and 0.65 g of ammonium chloride are dissolved in 20 ml of butanol. The reaction mixture is refluxed for 48 hours. The butanol is removed under vacuum and the residue is taken up in water and then extracted with ethyl acetate. The organic phase is separated off, dried over MgSO₄ and concentrated under vacuum. The residue is chromatographed on alumina using 5/5 (v/v) ethyl acetate/hexane and then 9/1 (v/v) ethyl acetate/methanol, with 2% of triethylamine added, as the eluent.

The pure product fractions are concentrated under vacuum to give 1 g of an oil, which crystallizes.

To prepare the fumarate, 0.54 g of fumaric acid is dissolved in 5 ml of acetone, and an acetone solution of 0.47 g of the base prepared above is then added. The crystals are filtered off to give 0.4 g of the expected fumarate.

M.p. = 148.2° C.

The compound described in Table 3 below is prepared by following the same procedure as for the previous examples.

TABLE 3

$$\text{Ph-C(CH}_3\text{)=... -NH-(CH)}_{n1}\text{-(CH)}_{n2}\text{-T}$$
(with Y₁ on (CH)n1 and Y₂ on (CH)n2; pyrazole ring N—N)

| Example n° | —(CH)$_{n1}$—(CH)$_{n2}$—T (with Y$_1$, Y$_2$) | Salt | Melting point; °C |
|---|---|---|---|
| 9 | —CH$_2$—CH(CH$_3$)—N(morpholino) | fumarate | 176 |

The pharmacological properties of the compounds according to the invention were studied, in particular their affinity for the muscarinic cholinergic receptors of the $M_1$ and $M_2$ type.

In vitro, the compounds (I) were tested using the technique described by L. POTTER et al., J. Pharmacol. Exp. Ther., 1989, 284, 974–978, as regards their affinity for the $M_1$ receptors, and using the technique described by HAMMER R. et al., Life Science, 1986, 38, 1653–1662, as regards their affinity for the $M_2$ receptors.

The compounds according to the invention have a good affinity for the $M_1$ receptors and a marked specificity for the $M_1$ central receptors compared with the $M_2$ receptors.

By way of example, the compounds I) according to the invention were found to have a 50% inhibitory concentration, expressed in nanomol per liter, of the order of 3.2 and 110 on the $M_1$ and $M_2$ receptors respectively.

In vivo, the compounds according to the invention were tested using the test for the rotations induced by intrastriatal pirenzepine, described by Worms P. et al., Psychopharmacology, 1987, 93, 489–493.

At a dose of 0.3 mg per kg of body weight, administered orally, the products according to the invention strongly inhibit the number of rotations induced by pirenzepine. Thus, by way of example, the compounds (I) according to the invention cause a 62% inhibition of the rotations induced by pirenzepine.

Consequently the compounds (I) can be used as drugs.

The compounds according to the invention have a good affinity for the muscarinic receptors and a good activity in the tests for the amnesia induced by scopolamine or pirenzepine. They make it possible to envisage using the products according to the invention in all cases where a cholinergic deficiency is in evidence, and especially for the treatment of cognitive memory disorders and degenerative syndromes associated with senescence and senile dementia.

Finally, the compounds according to the invention showed no sign of toxicity at the doses at which they are active.

According to another feature, the present patent application therefore relates to the pharmaceutically acceptable compositions containing at least one of the compounds of formula (I) or one of their salts as the active principle.

In the pharmaceutical compositions of the present invention for oral, sublingual, transdermal or rectal administration, the active principles of formula (I) above can be administered to humans in unit forms of administration, mixed with the conventional pharmaceutical carriers, especially for the treatment of cognitive memory disorders or degenerative syndromes. The appropriate unit forms of administration include forms for oral administration, such as tablets, gelatin capsules, powders, granules and solutions or suspensions to be taken orally, forms for sublingual and buccal administration, forms for subcutaneous, intramuscular or intravenous administration and forms for rectal administration.

To achieve the desired effect, the dose of active principle can vary between 0.5 and 500 mg per day.

Each unit dose can contain from 0.1 to 100 mg of active ingredient in combination with a pharmaceutical carrier. This unit dose can be administered 1 to 5 times per day.

When a solid composition is prepared in the form of tablets, the active principle is mixed with a pharmaceutical vehicle such as gelatin, starch, lactose, magnesium stearate, talc, gum arabic or the like. The tablets can be coated with sucrose or other appropriate substances or else they can be treated so as to have a prolonged or delayed activity and so as to release a predetermined amount of active principle continuously.

A preparation in the form of gelatin capsules is obtained by mixing the active principle with a diluent and pouring the mixture obtained into soft or hard gelatin capsules.

The water-dispersible granules or powders can contain the active principle mixed with dispersants or wetting agents or with suspending agents such as polyvinylpyrrolidone, as well as with sweeteners or taste correctors.

Rectal administration is effected using suppositories; these are prepared with binders which melt at the rectal temperature, for example cacao butter or polyethylene glycols.

Parenteral administration is effected using aqueous suspensions, isotonic saline solutions or sterile and injectable solutions which contain pharmacologically compatible dispersants and/or wetting agents, for example propylene glycol and butylene glycol.

The active principle can also be formulated as microcapsules, together with one or more carriers or additives if appropriate.

As a pharmaceutical preparation, it is possible to prepare gelatin capsules containing:

| | |
|---|---|
| Compound of Example 1 | 0.010 g |
| Lactose | 0.050 g |
| Magnesium stearate | 0.005 g |

What is claimed is:

1. A compound of the formula

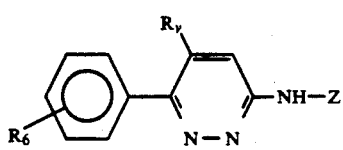

in which:

$R_Y$ is a linear or branched $C_1$–$C_4$ alkyl group;
$R_6$ is hydrogen, a $C_1$–$C_3$ alkoxy or a hydroxyl group; and Z is a group

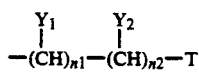

in which:

T is a heterocycle selected from:

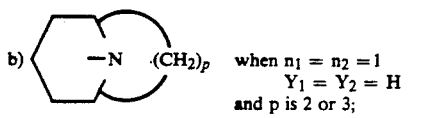  b) when $n_1 = n_2 = 1$
$Y_1 = Y_2 = H$
and p is 2 or 3;

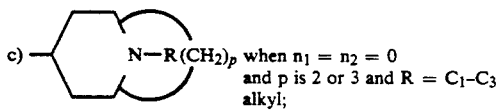  c) when $n_1 = n_2 = 0$
and p is 2 or 3 and $R = C_1-C_3$ alkyl;

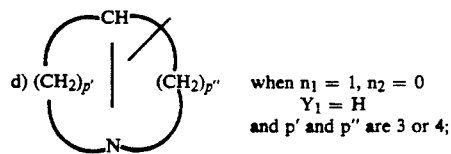  d) $(CH_2)_{p'}$ $(CH_2)_{p''}$ when $n_1 = 1, n_2 = 0$
$Y_1 = H$
and p' and p'' are 3 or 4;

and its pharmaceutically acceptable salts with organic or mineral acids.

2. A compound according to claim 1 wherein Z—N-H—is represented by the group N-8-azabicyclo[3,2,-1]octylethylamino, or one of its pharmaceutically acceptable salts.

3. A compound according to claim 1 wherein Z—N-H—is represented by the group 8-N-ethylazabicyclo[3,2,1]-octyl-3-amino, or one of its pharmaceutically acceptable salts.

4. A compound according to claim 1 wherein Z—N-H—is represented by the group 1-azabicyclo[3,3,0]octyl-2-methylamino, or one of its pharmaceutically acceptable salts.

5. A pharmaceutical composition containing, as the active principle, an effective amount of a compound of formula (I) according to claim 1, or a pharmaceutically acceptable salt thereof.

6. A pharmaceutical composition according to claim 5, in the form of a dosage unit, in which the active principle is mixed with at least one pharmaceutical excipient.

7. A composition according to claim 6 containing from 0.5 to 100 mg of active principle.

* * * * *

UNITED STATES PATENT AND TRADEMARK OFFICE
CERTIFICATE OF CORRECTION

PATENT NO. : 5,276,036

DATED : January 4, 1994

INVENTOR(S) : Jean-Jacques Bourguignon et al

It is certified that error appears in the above-indentified patent and that said Letters Patent is hereby corrected as shown below:

Column 2, line 66, change "$F_v$" to --$R_v$--.

Column 4, Scheme 2, change "$NH_2NH_2,N_2O$" to --$NH_2NH_2,H_2O$--.

Column 5, line 57, before "47" insert --24--.

Column 6, line 18, change "J. Med. Chem., 1987, 30, 1987" to --J. Med. Chem., 1985, 28, 714--.

Column 7, line 7, change "$n_1=n_2-1$" to --$n_1=n_2=1$--.

Column 9, line 55, change "1 52 g" to --1.52 g--.

UNITED STATES PATENT AND TRADEMARK OFFICE
CERTIFICATE OF CORRECTION

PATENT NO. : 5,276,036

DATED : January 4, 1994

INVENTOR(S) : Jean-Jacques Bourguignon et al

It is certified that error appears in the above-indentified patent and that said Letters Patent is hereby corrected as shown below:

IN THE CLAIMS:

Column 13,
Claim 1, between lines 11 and 13, insert the following two lines:

--$n_1$ and $n_2$ independently are zero or one,
$Y_1$ and $Y_2$ independently are hydrogen or a $C_1$-$C_3$ alkyl group, and--.

Signed and Sealed this

Sixth Day of September, 1994

BRUCE LEHMAN

*Attest:*

*Attesting Officer*              *Commissioner of Patents and Trademarks*